United States Patent [19]
Bolton et al.

[11] Patent Number: 5,798,217
[45] Date of Patent: Aug. 25, 1998

[54] METHOD OF ANALYZING TUMOR CELL DNA CONTENT THROUGH TUMOR CELL ENRICHMENT

[75] Inventors: Wade E. Bolton, Plantation; Norma Sue Kenyon, Miami; Olavi Siiman, Davie; Robert J. Schmittling, Cooper City, all of Fla.

[73] Assignee: Coulter Corporation, Miami, Fla.

[21] Appl. No.: 489,239

[22] Filed: Jun. 12, 1995

Related U.S. Application Data

[63] Continuation of Ser. No. 963,657, Apr. 26, 1993, abandoned.

[51] Int. Cl.$^6$ ............... G01N 33/574; G01N 33/53; G01N 33/555; G01N 33/567
[52] U.S. Cl. ............... 435/7.23; 435/2; 435/7.24; 435/962; 436/526; 436/236; 436/546; 436/548; 436/44; 436/172; 436/175; 356/39
[58] Field of Search ............... 435/7.23, 2, 7.24, 435/962, 6, 7.25; 436/526, 536, 546, 548, 44, 172, 175; 356/39

[56] References Cited

U.S. PATENT DOCUMENTS

| | | | |
|---|---|---|---|
| 3,864,212 | 2/1975 | Berkhan | 195/103.5 R |
| 4,423,153 | 12/1983 | Ranney et al. | 436/63 |
| 4,812,394 | 3/1989 | Dolbeare et al. | 435/6 |
| 4,885,237 | 12/1989 | Evans et al. | 435/6 |
| 5,018,209 | 5/1991 | Bacus | 382/6 |
| 5,223,398 | 6/1993 | Kortright et al. | 435/7.24 |

OTHER PUBLICATIONS van Dam, P.A. et al., Clin Pathol 43:833–839 1990.
Häcker-Shahin, B. et al., Transfers Sci 13:261–264 1992.
M. Raber et al., "DNA Flow Cytometry of Human Solid Tumors" in *Flow Cytometry and Sorting*, 2nd Ed. (Wiley-Liss, New York 1990) pp. 745–754.
T. Shankey, "Multiparameter Flow Cytometric Analysis of Bladder Cancer Specimens" Presented at: The Coulter Cytometry Midsest User's Meeting Arlington Hts., IL Feb. 1991.
J. C. van der Linden et al., Cytometry 13:163–168 (1992), "Flow Cytometric DNA Content of Fresh Tumor Specimens . . .".
M. Ferno et al., 13:241–249 (1992), "One or Multiple Samplings for Flow Cytometric DNA Analyses . . .".
O. Stal et al., Diagn. Oncol. 1:140–154 (1991), "DNA Analysis in the Management of Breast Cancer".

*Primary Examiner*—Sheela Huff
*Attorney, Agent, or Firm*—Howson and Howson

[57] ABSTRACT

The invention provides a method for enriching a sample in tumor cells and determining the DNA ploidy and proliferative index of the tumor cells present in the sample. The method uses a pan-leukocyte monoclonal antibody conjugated to a separable substrate such as magnetic microspheres to conjugate and remove leukocytes from the sample. A fluorescently labelled monoclonal antibody specific to a tumor associated antigen or an antigen arising from the presence of the tumor and a DNA staining reagent are added to the leukocyte depleted sample. The sample is then analyzed by dual color flow cytometry to determine cells having an abnormal DNA content by gating on fluorescently labelled cells.

13 Claims, 9 Drawing Sheets

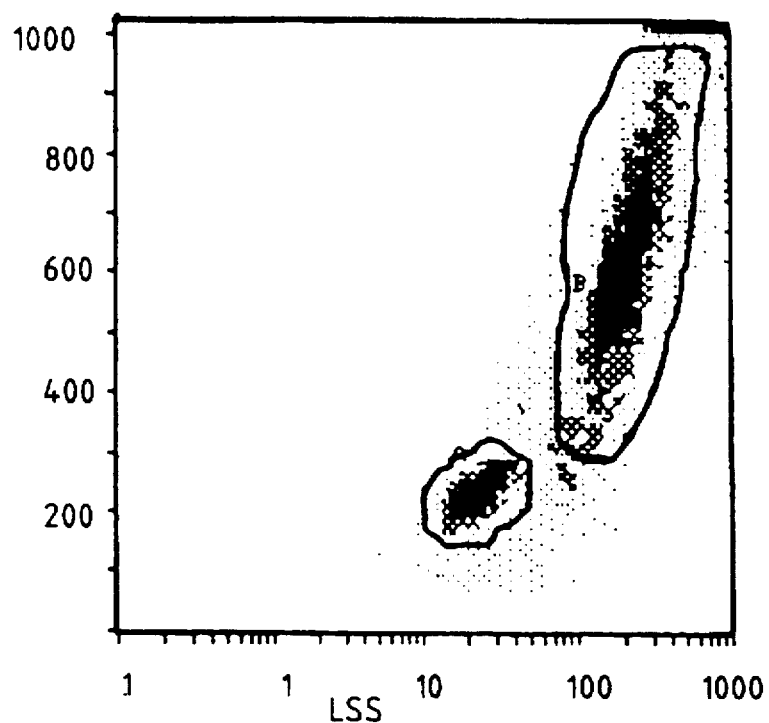
Fig. 2A NON-DEPLETED
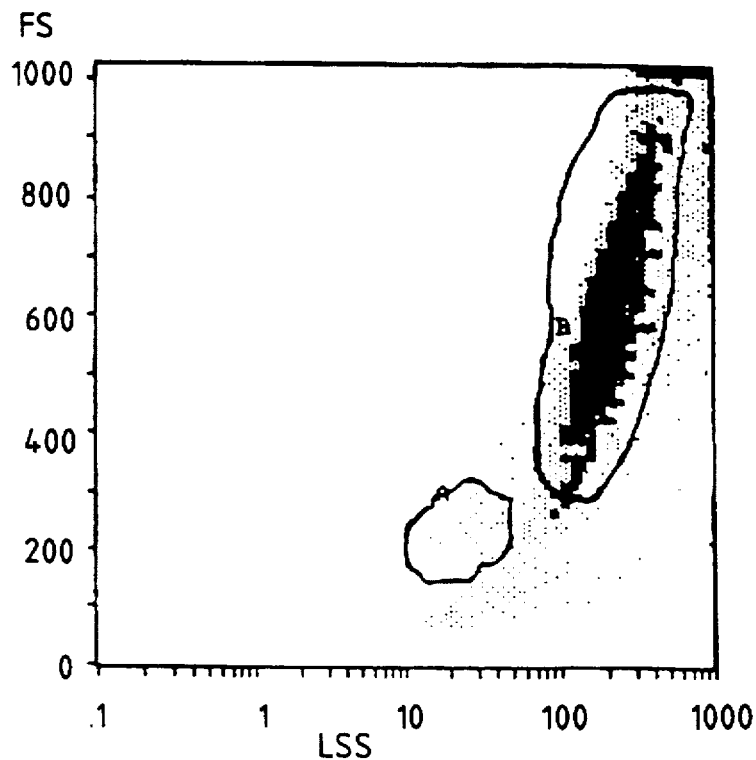
Fig. 2B DEPLETED

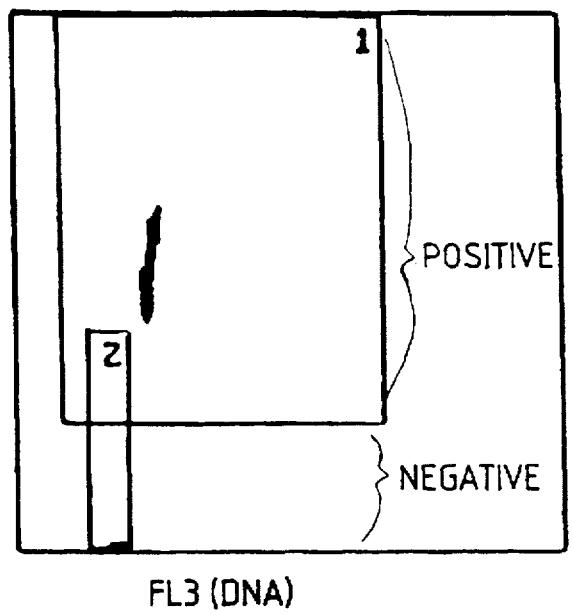
Fig. 3A NON-DEPLETED
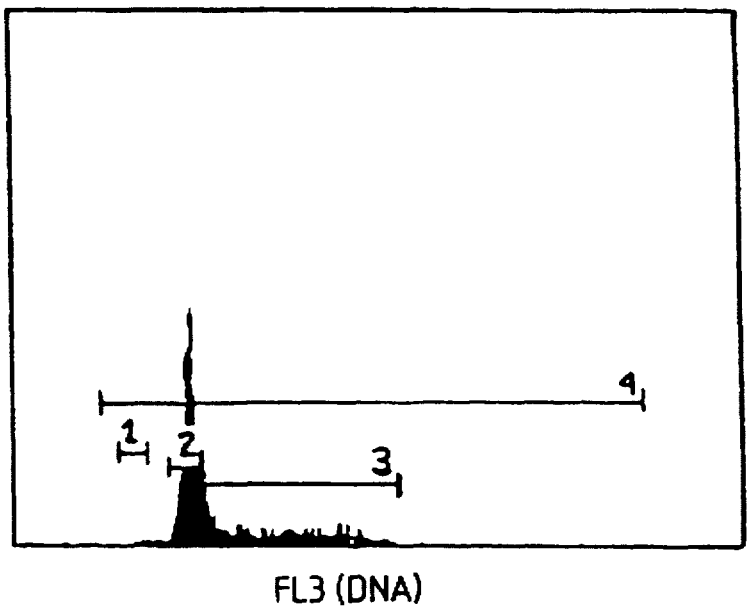
Fig. 3B NON-DEPLETED

Fig. 3C DEPLETED
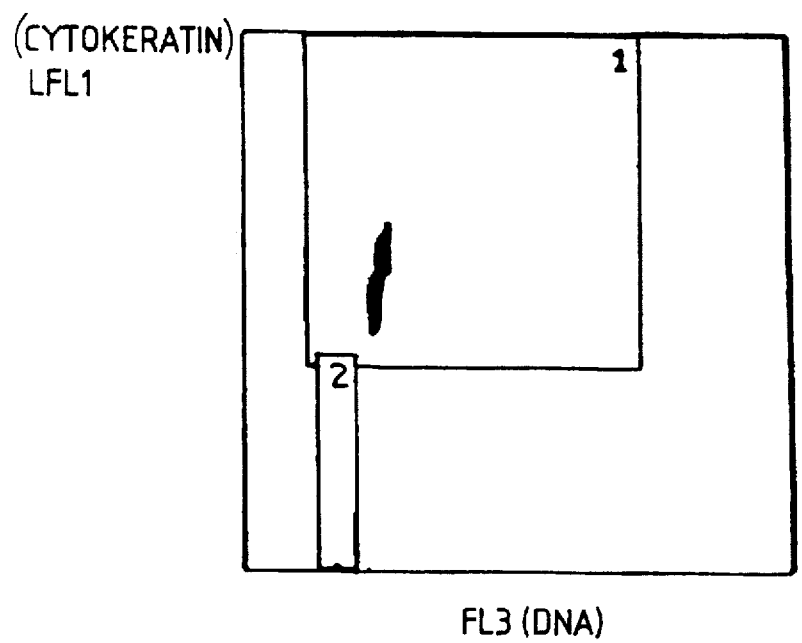
Fig. 3D DEPLETED
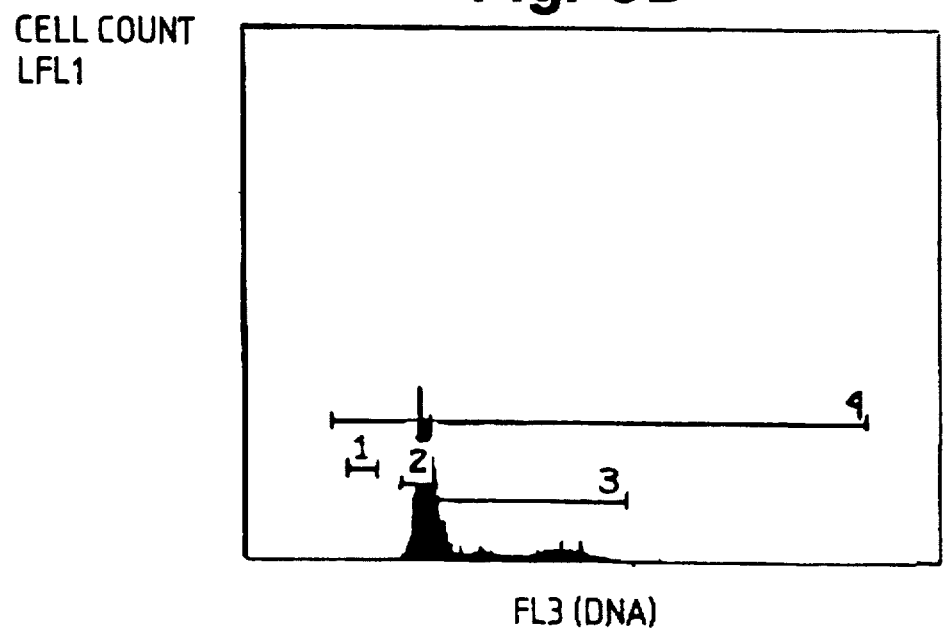

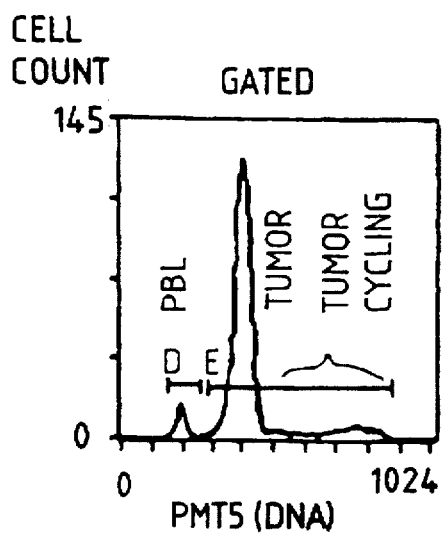
Fig. 4A NON-DEPLETED
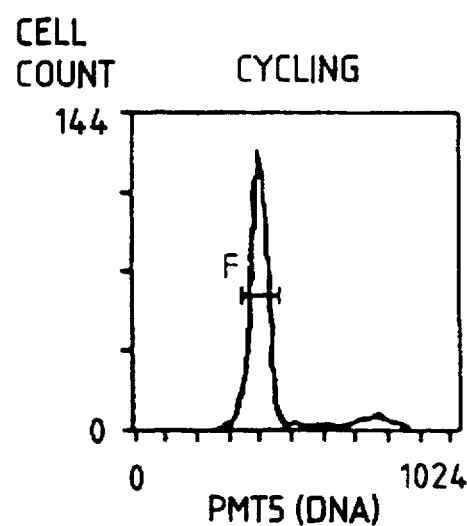
Fig. 4B NON-DEPLETED
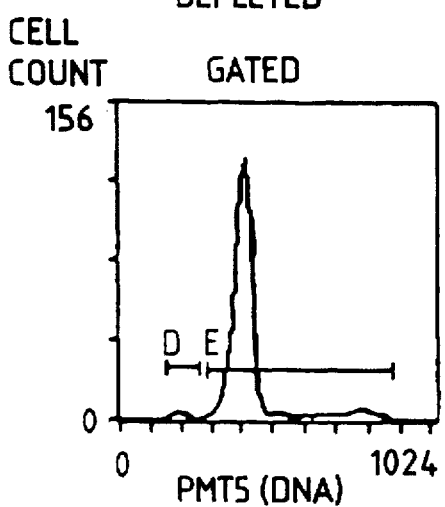
Fig. 4C DEPLETED
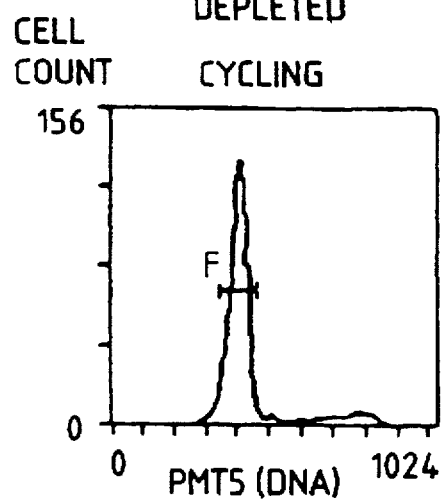
Fig. 4D DEPLETED

METHOD OF ANALYZING TUMOR CELL DNA CONTENT THROUGH TUMOR CELL ENRICHMENT

This is a continuation of application Ser. No. 07/963,657 filed on Apr. 26, 1993 now abandoned.

FIELD OF THE INVENTION

The present invention relates to a method for measuring DNA in a sample containing tumor cells. In particular, the invention relates to the use of a pan-leukocyte monoclonal antibody bound to a substrate to clear a sample of leukocytes present therein and thereby concentrate the tumor cells prior to DNA analysis.

BACKGROUND OF THE INVENTION

A cell sample derived from the preparation of a solid tumor sample for flow cytometric analysis may consist primarily of normal tissue components such as infiltrating leukocytes, fibroblasts and other normal cellular material. Tumor cells may constitute less than 10% of such a sample. In the conduct of a DNA analysis, these infiltrating cells and the normal, diploid cells can mask the presence of tumor cells with abnormal DNA/proliferative indices. As a result, the ability to detect, diagnose and treat the tumor is lessened.

U.S. Pat. Nos. 3,864,212 to Berkhan, 4,423,153 to Ranney et al., 4,812,394 to Dolbeare et al., 4,837,306 to Ling et al., 4,885,237 to Evans et al. and 5,018,209 to Bacus describe various methods of analyzing cellular DNA. Berkhan teaches treating cells for the measurement of DNA by digesting the cells in a solution of pepsin in hydrochloric acid before staining the DNA. Ranney et al. teach the use of a divalent metal cation and a fluorescent antibiotic, antineoplastic such as mithramycin, chromomycin or olivomycin in the presence of a surfactant and a membrane penetrating agent for the analysis of native, double stranded, helical DNA and for determining compounds which inhibit DNA-fluorochrome binding. Dolbeare et al. teach the use of flow cytometry to measure DNA and incorporated nucleoside analogs using an immunochemical staining agent such as ethidium bromide. Ling et al. teach monoclonal antibodies to a P-glycoprotein surface antigen correlated to multi-drug resistance. In Ling et al., the antibodies are used to obtain a cDNA probe which in turn is used to select a cDNA clone encoding for a portion of the P-glycoprotein. Evans et al. teach a method of detecting cells having newly synthesized DNA and for utilizing monoclonal antibodies to halodeoxyuridune (halodu) incorporated into newly synthesized DNA without destroying the cell morphology and antigens prior to binding the monoclonal antibody to the halodu. Bacus teaches a method and an apparatus for selecting and analyzing a subpopulation of cells for a parameter such as DNA or estrogen and then measuring the selected cells. For quantitative DNA analysis, Bacus measures the optical density of the cell object and the classification is done by a pathologist as to whether the cell is normal or cancerous. Bacus uses the term "cell object" to encompass non-biological objects such as conventional plastic or glass spheres used in biological studies, painted cell images on a slide, or antigens or monoclonal antibodies on cells.

The flow cytometric measurement of cells from human solid tumors has also been the subject of several publications. M. N. Raber et al., "DNA Flow Cytometry of Human Solid Tumors" in Flow Cytometry and Sorting, 2nd Ed., (Wiley-Liss, Inc. 1990) pages 745–754, provide a general background and discussion on the topic. O. Stal et al, Diag. Oncol., 1: 140–154 (1991) reviewed the relationships of DNA ploidy and S-phase fraction (proliferation fraction), and discussed the techniques used to measure DNA content in tumors. These techniques were the technique of Bargolie et al., Cancer Res., 38: 3333–3339 (1978), in which the tumor tissue is desegregated by mechanical means and pepsin treatment followed by fixation in ethanol and staining with ethidium bromide and mithramycin; the technique of Thornwaite et al., Cytometry, 1: 229–237 (1980), in which the tissue is stretched or minced in a phosphate buffer solution containing the detergent NP40 and one of the fluorochromes propidium iodide or diamidinophenylindole; and the method of Vindelöv et al., Cytometry, 3: 323–327 (1983), in which trypsin is used in addition to the detergent NP40.

A convention has been settled upon for stating the abnormal DNA content in cells. The DNA index (DI) is calculated by dividing the modal DNA content of the population of cells being analyzed by the DNA content of the corresponding normal cells. Samples which have a DNA content equal to those of normal cells are given a DI=1 and are called diploid cells. Cells which have a non-normal DNA content are called aneuploid cells. The aneuploid cells may be of two types. Aneuploid cells with DI<1 are called hypodiploid and those with DI>1 are called hyperdiploid. Hyperdiploid cells with DI=2 are given the special name of tetraploid.

Raber et al., op. cit., state that care must be taken with samples in which there is a minimum deviation aneuploidy, DI=0.95–1.05. In situations where there is one peak in the diploid range with a high coefficient of variation (CV), the analysis should be repeated using different fluorochromes. A difficulty arises in these situations from the presence of the diploid peak which may mask hidden, near-diploid, aneuploid peaks.

After the analysis of over 7,000 solid tumor samples, Raber et al. have found that an aneuploid population is found in over 70% of the tumors. They concluded that aneuploidy is an excellent marker for malignant cell populations and that the DNA index is found to correlate well with chromosome number as determined by karyotypic analysis in both leukemias and solid tumors. The fact that a higher number of tumors have not been found aneuploid stems from the limits of resolution in DNA content analysis and from tumors which have undergone translocation or other genomic changes that are not reflected in DNA content or chromosome number. A variation of 0.05 in the DNA index represents one chromosome. The DNA histogram that is obtained from the flow cytometric analysis is used to determine the S-phase fraction (SPF), also called the proliferative index. These are the cells which actually replicate.

J. C. van der Linden et al., Cytometry, 13: 163–168 (1992), describe two parameter flow cytometric DNA analysis. Tumor samples are homogenized in Minimal Essential Medium, filtered through nylon gauze, centrifuged and the supernatant removed and discarded. The resulting cell pellets were fixed in ethanol and stored a minimum of 48 hours. After cell counting and concentration adjusting, chicken red blood cells were added as an internal standard, the resulting sample was centrifuged, and the cells washed and recentrifuged. The resulting cell pellets were then incubated with mouse anti-human cytokeratin. A second incubation was performed with fluorescein conjugated rabbit anti-mouse serum. After washing and pelleting, the cells were stained with propidium iodide containing RNase. The resulting cells were kept in the dark for at least 24 hours prior to flow cytometric analysis. A similar method of analysis is described by Marten Ferno et al., Cytometry 13: 241–249 (1992).

T. V. Shankey in an oral and written presentation titled "Multiparameter Flow Cytometric Analysis of Bladder Cancer Specimens", given at the Coulter Cytometry Midwest User's Meeting, Arlington Heights, Ill., February 1991, presented the basic concepts and some limitations of single parameter DNA content measurements. Shankey reported that the major problem for flow cytometric measurements of TCC (transitional cell carcinoma of the bladder) is the presence of large numbers of reactive cells such as neutrophils and macrophages, red blood cells and necrotic cells in the sample. Shankey identified some of the markers or labels which have been used by various investigators in attempts to improve the ability to detect bladder tumor cells from exfoliated specimens. Shankey identified some of the markers or labels which have been used by various investigators in attempts to improve the ability to detect bladder tumor cells from exfoliated specimen. Shankey found the use of monoclonal antibodies promising; but he finds that [a problem arises] because "Many monoclonal antibodies which react with transitional cell tumors also react with normal cells found in the urogenital tract. An additional problem is that monoclonals frequently react with high grade tumors and not low grade TCC. Since most high grade tumors are DNA aneuploid, the use of these antibodies provides little improved sensitivity in the detection of exfoliated bladder tumors".

The present invention describes a method of cellular DNA analysis which overcomes the shortcomings of the prior art. The use of the claimed method permits a more accurate measure of the ploidy of cells present in a tumor and a more accurate determination of the proliferative index.

SUMMARY OF THE INVENTION

The invention provides a method for the analysis of DNA containing tumor cells in a sample containing or thought to contain such cells by the use of a selective monoclonal antibody conjugated to a discrete particulate support or substrate to deplete the sample of cells which may mask or interfere with the analysis of such DNA containing cells, a second detectably labelled monoclonal antibody and a dye which will stain DNA, and gated flow cytometric analysis of the sample. Such cell samples may have less than 10% tumor cells and may consist primarily of normal tissue components such as infiltrating leukocytes, fibroblasts and other normal cellular material. The method uses the first monoclonal antibody, which is selective to leukocytes and preferably conjugated to magnetic microspheres to substantially remove normal leukocytes from the sample. The leukocyte depleted sample is then incubated with a second selective monoclonal antibody which has a fluorescing label attached thereto. The second monoclonal antibody may either specifically bind to a tumor associated antigen or it may bind to a tissue associated antigen from which the tumor has arisen (cytokeratin). A DNA staining dye is then added to the sample. Subsequently, the sample is analyzed by dual color flow cytometry to specifically analyze the cells for DNA content by gating on the fluorescently labelled tumor cells.

BRIEF DESCRIPTION OF THE DRAWINGS

FIGS. 2 (A and B) illustrate, respectively, the light scatter histograms of depleted and undepleted 1:1 PBL/SW1116 samples.

FIG. 3 (A and C) are light scatter histograms reflecting the cytokeratin activity of depleted and undepleted, respectively, 1:1 samples.

FIGS. 3 (B and D) are DNA histograms reflecting the cytokeratin activity of depleted and undepleted, respectively, 1:1 samples.

FIGS. 4 (A and C) are single parameter histograms of the total DNA present in a breast tumor sample containing 5% PBLs before and after PBL depletions, respectively.

FIGS. 4 (B and D) are single parameter histograms representing the DNA cytokeratin positive cells in a breast tumor sample containing 5% PBLs before and after PBL depletion, respectively.

FIGS. 5 (B and D) are single parameter histograms representing the DNA of cytokeratin positive cells in a breast tumor sample containing 25% PBLs before and after PBL depletion, respectively.

FIGS. 6 (B and D) are single histograms representing the DNA of cytokeratin positive cells in a breast tumor sample containing 75% PBLs before and after depletion, respectively.

FIGS. 7 (B and D) are single parameter histograms representing the DNA of cytokeratin positive cells in a breast tumor sample containing 95% PBLs before and after PBL depletion, respectively.

DETAILED DESCRIPTION OF THE INVENTION

Figure 1A:
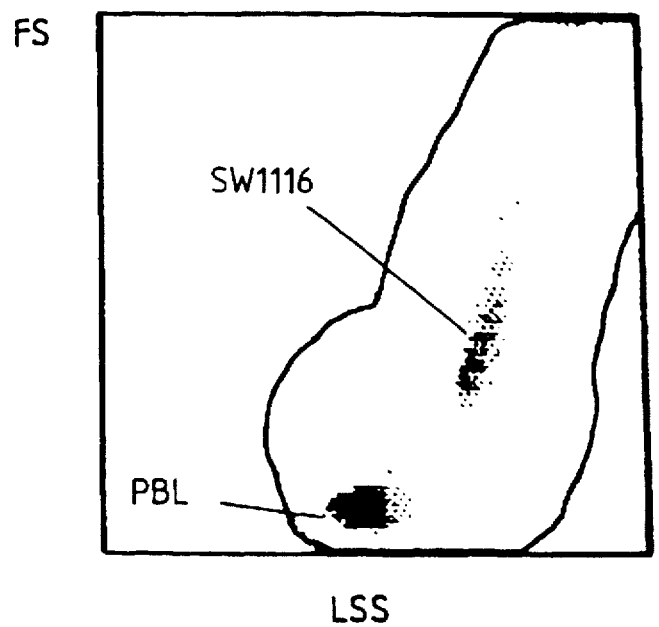
FIGS. 1 (A and B) illustrate, respectively, the light scatter and DNA histograms of a 1:1 PBL/SW1116 mixture before treatment.

Proliferative assessment of tissue tumor cells can be hindered by the presence of infiltrating leukocytes and other normal tissue components which can mask the presence of aneuploid and/or proliferating tumor cell populations. According to the claimed invention, a sample is first incubated with a pan-leukocyte specific monoclonal antibody such as an anti-CD45 monoclonal antibody conjugated to discrete particles, preferably magnetic microspheres. After incubation for a sufficient time of about 0.25 to about 2.0 hours, the microspheres are removed from the sample, thereby removing from the sample the infiltrating leukocytes which have conjugated with the pan-leukocyte antibody.

Removal of the infiltrating leukocyte cells enriches the sample for tumor cells. The infiltrating leukocytes that are removed include lymphocytes, granulocytes, monocytes and macrophages. In a mixed population of cells consisting of, for example, 85% peripheral blood leukocytes, 10% normal fibroblasts (WI-38) and 5% breast tumor cells (MDA-Mb-175-VII), 95% of the infiltrating leukocytes were depleted using an anti-CD45 monoclonal antibody conjugated to magnetic microspheres. Typically, the tumor cells in such a mixed sample may be enriched from about 5% to about 50%, or more prior to DNA analysis and determination of the tumor cell's proliferative activity. The use of a microsphere bound pan-leukocyte monoclonal antibody replaces the need to treat a heterologous tumor cell sample with a labelled pan-leukocyte monoclonal antibody and separate the labelled cells from other cells in the cytometer via cell sorting of gating. It decreases the total number of cells which must be counted in order to obtain a valid DNA analysis. The use of the microsphere bound antibody thereby simplifies the analytical process and allows for the depletion of any cell type for which a specific monoclonal antibody, DNA probe or other specific reagent or probe exists.

After depletion of leukocytes, the tumor enriched sample may still contain normal tissue components which will interfere with the tumor cell analysis. For example, the sample may contain fibroblasts from connective tissue. The sample is, therefore, first incubated with a fluorescently labelled monoclonal antibody directed to either a tumor associated antigen such as Mc5 or CEA, or directed to a tissue associated antigen from which the tumor has arisen (cytokeratin, permeabilization is required prior to staining). The cells are then permeabilized and a DNA staining agent, for example, propylium (propidium) iodide or ethidium bromide, is added to stain the DNA. Alternatively, the cells are not permeabilized and a DNA staining agent capable of penetrating the cell wall, for example, hydroethidium, is used to stain the DNA. The sample is then analyzed by dual color flow cytometry. Abnormal DNA is determined by gating on the fluorescently labelled tumor cells. The presence of other normal cell types can be confirmed through flow cytometric analysis by gating on cells labelled with monoclonal antibodies specific for such cells; for example, fibroblasts.

The term "tumor associated antigen" and the phrase "tissue associated antigen from which the tumor has arisen (cytokeratin)" have the following meaning. A tumor associated antigen is one that specifically distinguishes a malignant from a normal cell. Most tumor specific markers or antibodies presently known react with normal cells in addition to reacting with malignant cells. For example, the Mc5 antigen is referred to as a tumor associated antigen. In fact, Mc5 is actually present in both normal and malignant breast epithelial cells. However, if a tumor is actually present, the percentage of Mc5 positive cells will be increased. The increase occurs because carcinomas are of epithelial origin and epithelial cells are not normally the majority of cells in the breast. The presence of Mc5 reactivity in a lymph node will indicate metastatic breast carcinoma.

In contrast to a tumor associated antigen such as Mc5, cytokeratin is a tissue associated antigen. Cytokeratin is present in all normal and malignant cells of epithelial origin, in contrast to Mc5 which is present only in breast epithelial cells. The presence of cytokeratin in a lymph node would indicate metastatic carcinoma, but it would not predict the tissue in which the carcinoma has arisen; for example, breast or colon. As used herein, the terms "labelled monoclonal antibody" or "second monoclonal antibody" refer to an antibody to such tumor and tissue antigens.

DETAILED DESCRIPTION OF THE PREFERRED EMBODIMENTS

The following examples are given to illustrate the preferred embodiments of the invention. The examples are not to be taken as limiting or restricting the scope of the invention. Substitution of the specific monoclonal antibodies or DNA staining agents described herein by other monoclonal antibodies or staining agents having the defined properties and available from other sources is to be understood as being within the ability of those skilled in the art. The use of fluorescently labelled DNA probes, for example, a FITC labelled probe specific for an oncogene, oncogene product, and other specific cell markers, for example, estrogen, may also be used according to the invention to identify specific cell populations. The invention also is not to be limited to tumor cells from any specific bodily tissue or organ. It is applicable to any tumor which contains infiltrating leukocytes or any tumor for which a tumor associated or tissue associated monoclonal antibody is available. Furthermore, the invention also is applicable to DNA analysis for tumor cells arising from lymphomas or leukemias. However, in performing an analysis of cells arising from leukemia or lymphoma, the leukocyte depletion step utilizing the pan-leukocyte monoclonal antibody conjugated to magnetic microspheres or other particulate substrate would be omitted, in cases where the leukemia cells are CD45 positive, and the actual first step of the analysis would be treating the lymphoma or leukemia sample with the labelled monoclonal antibody and the DNA staining agent.

Solid tumor samples which are to be analysed according to claimed invention may be treated to obtain single cell suspensions and subsequently processed using the Coulter® DNA-Prep Reagent System and Workstation, or equivalent, which automatically prepares single cell or nuclei suspensions for flow cytometric analysis of DNA content by lysing red blood cells (RBCs), permeabilizing cells, and adding DNA binding dye and RNase. Alternative methods of lysing erythrocytes permeabilizing cells, removing RNA and staining for DNA are known and may be used to stain single cell suspensions for analysis according to the claimed invention.

The term "gating" refers to the use of the software capabilities of the flow cytometer which thereby enable the user to determine the population or count of a selected subset of cells within a selected set of cells without having to physically separate the set and subset of cells as could be done using cell sorting techniques. For example, using the gating technique, cytokeratin positive cells can be counted and the DNA content of the cells determined. In the analysis of a mixture of normal and malignant cells, multiple steps can be used to give a detailed analysis of the cells present. For example, a sample obtained from a breast tumor can first be analyzed by gating using the monoclonal antibody Mc5 to identify both malignant and normal epithelial cells. A second gating on estrogen positive cells is then used to determine ploidy and proliferative index. These gatings are done sequentially without separating the epithelial cells from the bulk sample between gatings.

The anti-CD45 monoclonal antibody KC-56 or KC-56-FITC (FITC=fluoroscein isothiocyanate) and erythrocyte specific monoclonal antibody KC-16 or KC-16-FITC is available from Coulter Immunology, Hialeah, Fla. The KC-56 and KC-16 antibodies bound to magnetic microspheres may also be obtained from Coulter Immunology or the antibodies may be separately purchased and bound to the magnetic microspheres, or other substrate, by the user. For example, a substrate may be coated with goat anti-mouse immunoglobulin (GAM) or rabbit anti-mouse immunoglobulin (RAM) and the antibody bound thereto as described in U.S. Pat. No. 4,752,563 which is incorporated herein by reference, or the antibody and the substrate may be separately functionalized to contain reactive thiol and maleimidyl groups and then joined by the reaction of such groups.

GAM, GAM-FITC, RAM, RAM-FITC, G1, G1-FITC (mouse immunoglobulin G1), anti-cytokeratin anti-cytokeratin-FITC, Mc5, Mc5-FITC, CEA and CEA-FITC are also available from Coulter Immunology. The cell line SW 1116 is available from the American Type Culture Collection, Rockville, Md., ATCC deposit number CCL 233. SW 1116 is from a Grade II adenocarcinoma of the colon extending into the muscularis. The cells contain high levels of the tumor marker CEA (carcinoembryonic antigen) and are cytokeratin positive, CD45 negative. The cell line MDA-MB-175-VII is available from the ATCC, deposit number HTB 25. MDA-MB-175-VII is a breast carcinoma cell line derived from a pleural effusion and is CEA, Mc5 and cytokeratin positive and CD45 negative. The cell line WI-38 is available from the ATCC, deposit number CRL-75. WI38 is a fibroblast cell line derived from human lung tissue. The cells are cytokeratin, CEA, Mc5 and CD45 negative.

EXAMPLE 1

A sample representative of a colon tumor infiltrated with lymphocytes was prepared by mixing SW 1116 cells and normal peripheral blood leukocytes (PBL) which consist primarily of lymphocytes and monocytes obtained by density gradient centrifugation over Ficoll-Hypaque®. DNA analysis of the tumor cells was performed after first depleting the sample of leukocytes by using an anti-CD45 monoclonal antibody conjugated to magnetic microspheres. The leukocyte depleted sample is then treated with a tissue associated monoclonal antibody, in this instance an anti-cytokeratin monoclonal antibody, to positively identify the tumor cells and enable them to be counted. The quantity of microspheres, either by weight or volume, required to completely deplete a 1:1 cell/cell PBL/SW 1116 sample was experimentally determined. The exact quantity of microspheres required for 100% PBL depletion is a function of the antibody concentration of the microspheres and the total leukocyte count of the sample. Similar experimental determinations were made with samples having PBL/SW 1116 cell/cell ratios of 9:1, 7.5:2.5, 2.5:7.5, 1:9 and 0:10.

Sample tubes were prepared containing (a) $4 \times 10^6$ PBLs, (b) $4 \times 10^6$ SW 1116 cells and (c) $2 \times 10^6$ PBLs plus $2 \times 10^6$ SW 1116 cells at a concentration of $10 \times 10^6$ cells/ml in phosphate buffered saline solution containing 1% fetal calf serum (hereafter PBSF). Two sets of tubes having one each of (a), (b) and (c) were used in the following steps.

Magnetic microspheres having a known concentration of an anti-CD45 monoclonal antibody (KC-56) were washed twice with PBSF. A predetermined amount of anti-CD45 conjugated microspheres sufficient to deplete all the leukocytes of (a) was added to one set of tubes (hereafter the depleted set). Sufficient PBSF was added to the second set of tubes, hereafter the nondepleted set, so that the volumes of the tubes in the depleted and nondepleted sets were equal, and the nondepleted set was stored at 2°-8° C. during magnetic microsphere treatment of the depleted set. The tubes were then mixed at room temperature (18°-27° C.) for about 15 minutes using a rocker mixer. Following mixing, the samples were diluted with six volumes of PBSF and the microsphere containing set was placed in a magnetic device for three minutes. Cells bound to the anti-CD45 conjugated microspheres, CD45 positive cells, were drawn to the side of the sample tube during the magnetic separation and CD45 negative cells remained in suspension. The supernatant liquids were withdrawn from the depleted set, transferred to new sample tubes and centrifuged to obtain cell pellets (3 undepleted and 3 depleted).

As a general technique, the cell pellets were resuspended in phosphate buffered saline (PBS) and the cells counted using a hemacytometer. Aliquots of the suspension were prepared and processed for staining with tumor and tissue associated monoclonal antibodies by standard techniques. Either direct or indirect staining procedures may be used. As an example of an indirect procedure, the first monoclonal antibody is either an unlabelled isotype control antibody or an unlabelled antibody to a tumor or tissue associated antigen, for example, an anti-cytokeratin monoclonal antibody. The sample is then incubated with goat anti-mouse immunoglobulin conjugated to a fluorescent dye, for example, fluorescein, to enable detection of specifically labelled cells. In the direct procedure; the control and the monoclonal antibodies are labelled with the fluorescing dye.

In this example, after cell counting using the hemacytometer, the samples were recentrifuged and the cells in each resulting pellet were permeabilized by addition of 1 ml of 0° C. absolute methanol per sample tube and incubation for about five minutes at 0° C. The samples were again centrifuged and the resulting cell samples from both sets were washed with PBSF. Cells from each set of tubes were divided into two aliquots; i.e., a-c of both the depleted and nondepleted samples were divided into 2 aliquots having approximately $10^6$ cells/tube (although tube (a) should be empty in the depleted set). One aliquot from each sample was incubated with the control antibody, IgG1, and the other aliquot was incubated with an anti-cytokeratin monoclonal antibody. Incubation was at room temperature for about fifteen minutes. All cell samples were then centrifuged, washed with PBSF, resuspended in PBSF, incubated with GAM-FITC at room temperature for about fifteen minutes, recentrifuged and washed with PBSF. The resulting cell samples were then resuspended in 1 ml of propidium iodide staining solution for about 10 minutes at room temperature and subsequently analyzed by optical microscopy and flow cytometry. The analytical results as shown in Table 1 indicate PBLs can be substantially depleted from a PBL containing cell sample by use of a pan-leukocyte monoclonal antibody conjugated to microspheres, thus enriching the sample for cytokeratin positive tumor cells.

TABLE 1

| Optical Microscopy, Cytokeratin stained cells | | |
|---|---|---|
| | PBL | SW 1116 |
| KC-56 Depleted 1:1 mixture | 10 | 129 |
| Undepleted 1:1 Mixture | 121 | 116 |

The cytometric results, FIG. 1-3, 1:1 PBL/SW1116 samples, indicate that the PBL depleted samples will be enriched in cytokeratin positive cells. That is, a higher percentage of the cells in the PBL depleted samples will be cytokeratin positive relative to the percentage in the undepleted sample.

Figure 1B:
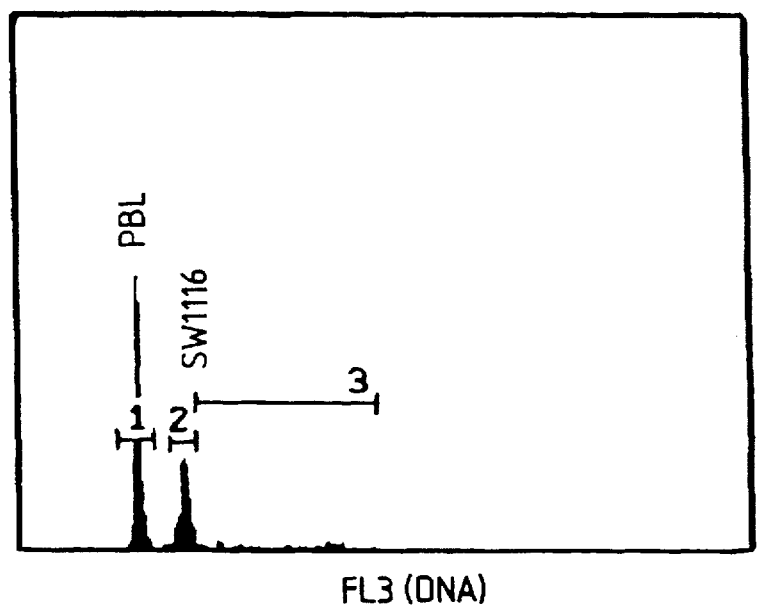
Figure 5A:
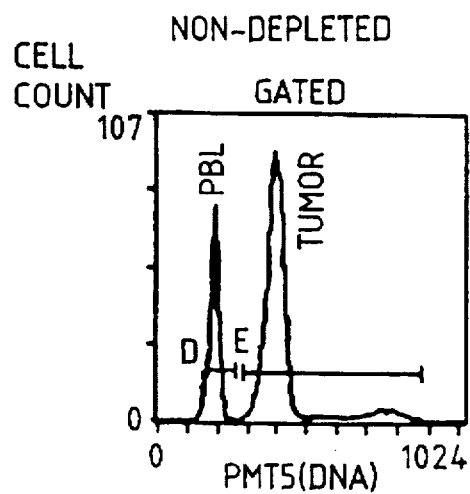
FIGS. 5 (A and C) are single parameter histograms of the total DNA present in a breast tumor sample containing 25% PBLs before and after PBL depletion, respectively.
Figure 5B:
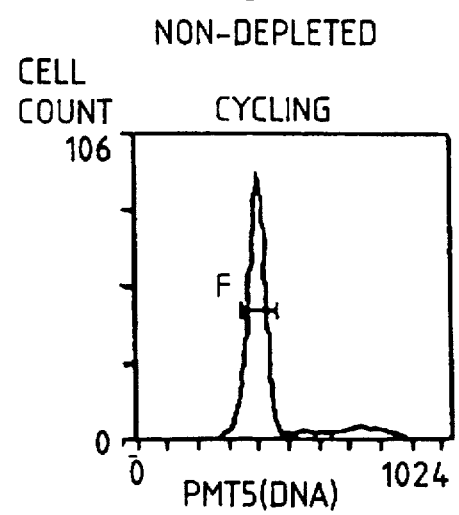
Figure 5C:
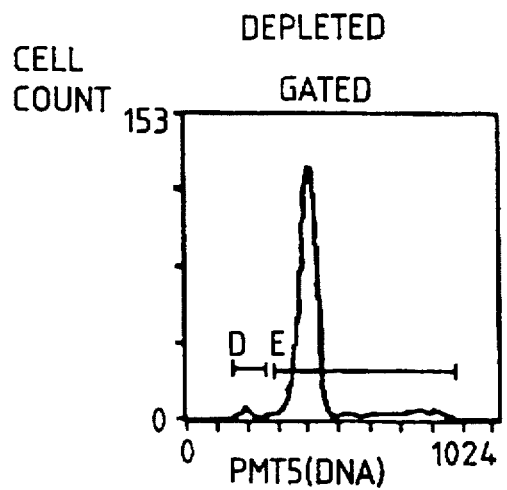
Figure 5D:
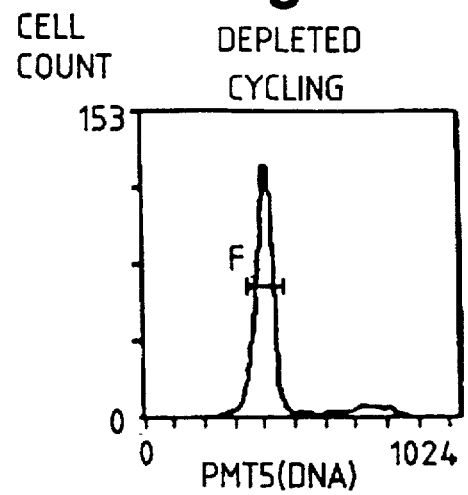
Figure 6A:
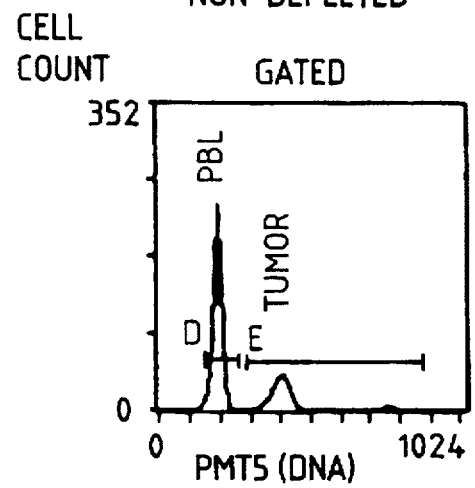
FIGS. 6 (A and C) are single parameter histograms of the total DNA present in a breast tumor sample containing 75% PBLs before and after PBL depletion, respectively.
Figure 6B:
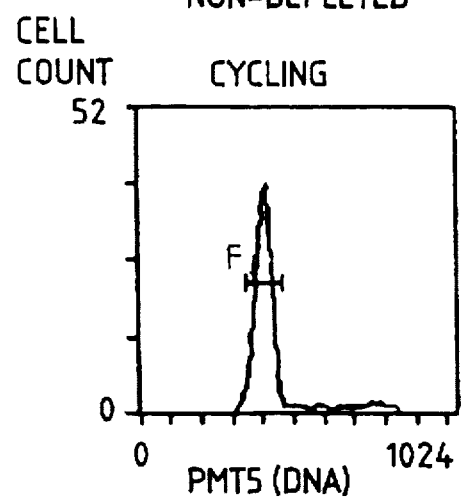
Figure 6C:
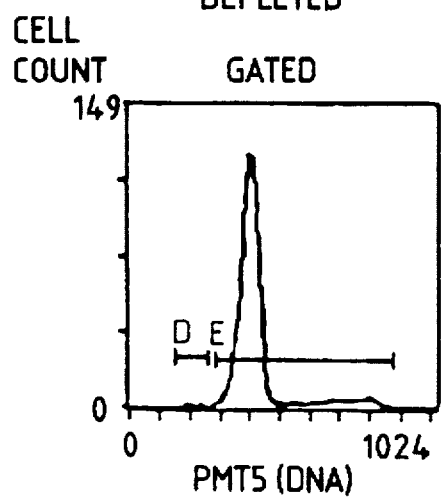
Figure 6D:
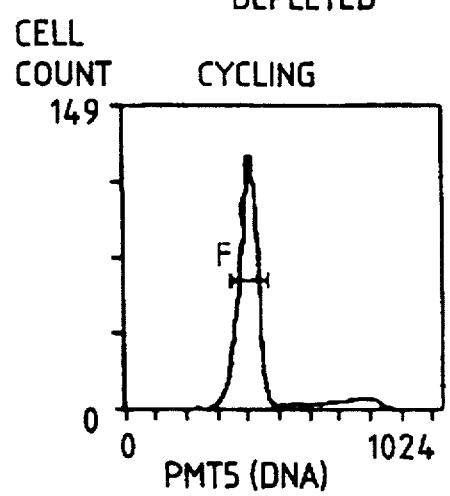
Figure 7A:
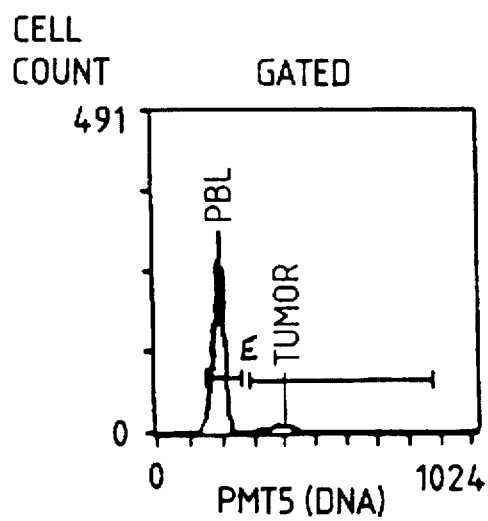
FIGS. 7 (A and C) are single parameter histograms of the total DNA present in a breast tumor sample containing 95 PBLs before and after PBL depletion, respectively.
Figure 7B:
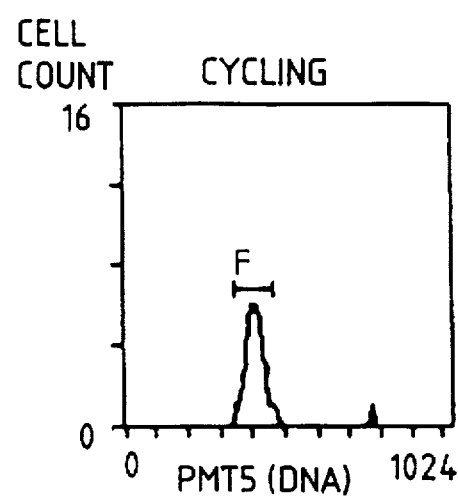
Figure 7C:
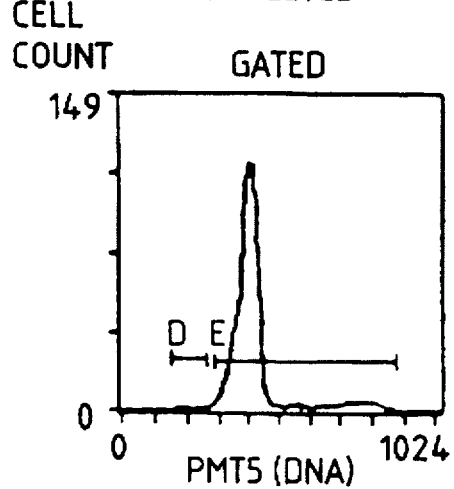
Figure 7D:
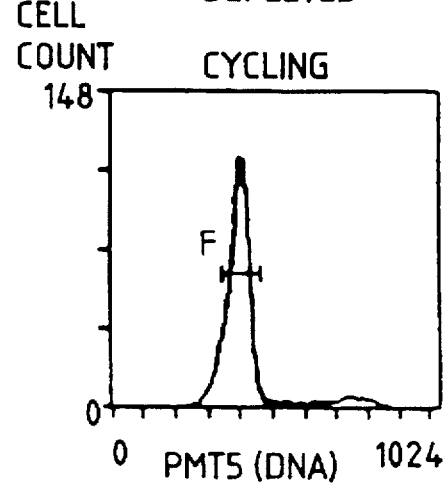
Figure 8A:
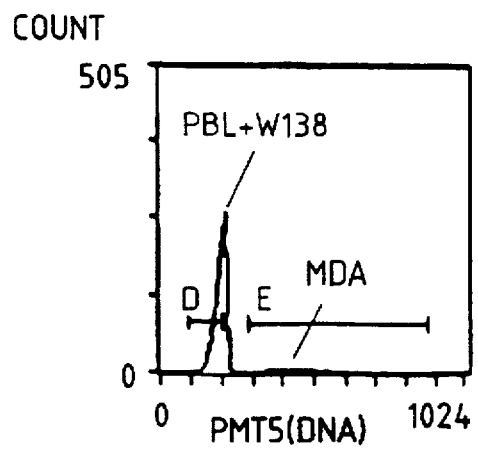
FIG. 8A is the undepleted histogram a sample representative of a breast tumor preparation which contains 85% PBLs, 5% MDA-MD-175-VII cells (breast tumor) and 10% WI-38 (normal fibroblast) cell.
Figure 8B:
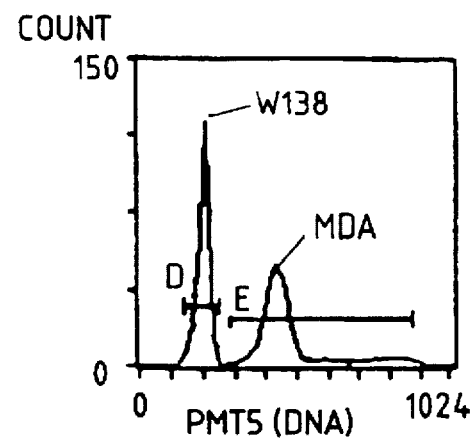
FIG. 8B is the histogram of a sample corresponding to that of FIG. 8A which has been PBL depleted using an anti-CD45 monoclonal antibody.
Figure 8C:
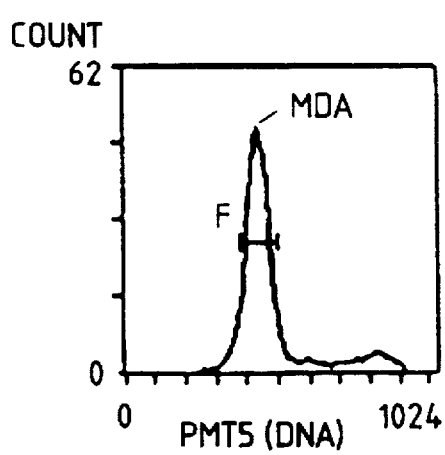
FIG. 8C is the histogram of a sample corresponding to that of FIG. 8A which has been subsequently PBL depleted, using an anti-CD45 monoclonal, and anti-cytokeratin treated.
Figure 8D:
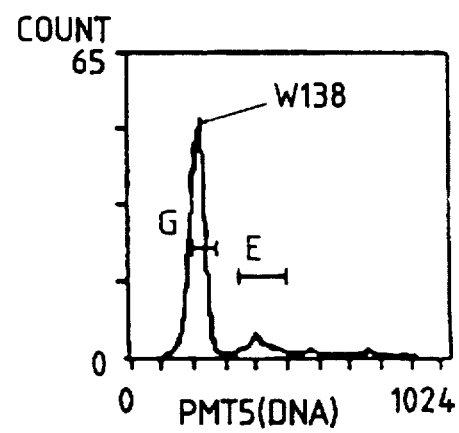
FIG. 8D is a histogram of a sample corresponding to that of FIG. 8A which has been subsequently PBL depleted, using an anti-CD45 monoclonal antibody, and anti-fibroblast treated.

FIGS. 1A and 1B represent the light scatter and DNA histograms of the 1:1 PBL/SW1116 mixture before any treatment. The two cell types are readily distinguishable in both the light scatter and the DNA analysis. The DNA peak due to PBLs was previously identified by gated DNA analysis of anti-CD45 (KC-56) positive cells (results not shown). The cycling DNA of the SW 1116 cells was similarly determined in separate experiments by gating on cytokeratin positive cells (results not shown).

FIGS. 2A and 2B represent the light scatter histograms of the depleted and undepleted 1:1 PBL/SW 1116 samples. The light scatter analysis above clearly indicates that PBLs can be substantially depleted from a sample by the use of a pan-leukocyte monoclonal antibody bound to separable substrate such as microspheres.

FIGS. 3A–3D represent the light scatter (A and C) and DNA (B and D) histograms reflecting the cytokeratin activity of the depleted (A and B) and undepleted (C and D) 1:1 samples. The percent cytokeratin cells is increased in the depleted sample. The PBL DNA peak is not present in the nondepleted histograms because only cytokeratin positive cells were analyzed. These histograms clearly demonstrate the utility of gated DNA analysis for cell sample having a mixture of cell types.

EXAMPLE 2

Samples representative of a breast tumor infiltrated with lymphocyte cells were prepared by mixing MDA-MB-175-VIII breast tumor cells with PBLs. Samples containing 5%, 25%, 75% and 95% PBLs were prepared. As in Example 1, two sets of sample tubes were prepared, one set to be the undepleted control and the other to be depleted as described herein. Each set contained all four PBL/tumor cell mixtures. PBL depletion was done using an anti-CD45 monoclonal antibody (KC-56) conjugated to magnetic microspheres according to the procedure described herein. A direct immunofluoresce staining procedure was used in place of the indirect method described in Example 1. Non-permeable cells were stained using KC56-FITC and permeabilized cells were stained with anti-cytokeratin-FITC. Isotype controls were used for all antibodies. The permeabilized samples were prepared using a Coulter DNA-Prep® workstation (Coulter Corporation, Hialeah Fla.) which automatically permeabilizes, lyses red blood cells, eliminates RNA and stains DNA. The KC-56 stained samples were flow cytometrically analyzed for FITC fluorescence. The anti-cytokeratin stained cells were analyzed by dual parameter flow cytometry for FITC fluorescence and DNA.

The results shown in Table 2 and FIGS. 4–7 clearly indicate that infiltrating lymphocytes can be depleted from a cell sample using antibodies conjugated to microspheres. Further, it is evident that gated DNA analysis of the cytokeratin positive cells clearly identifies tumor cells in a sample, even when the tumor cells constituted only 5% of the total cells in the original sample. Lastly, while it is difficult to discern cycling tumor cells in a sample containing 5% total tumor cells, the cycling tumor cells are readily identified after PBL depletion.

TABLE 2

| Characterization of Tumor Cells in a Sample Before and After PBL Depletion | | | | |
|---|---|---|---|---|
| Initial % PBLs | % CD45 Positive Cells | % Cytokeratin Positive Cells | % PBLs Depleted | % Tumor Enrichment |
| UNDEPLETED SAMPLES | | | | |
| 5 | 9.6 | 94.9 | — | — |
| 25 | 23.0 | 76.1 | — | — |
| 75 | 65.9 | 30.2 | — | — |

TABLE 2-continued

| Characterization of Tumor Cells in a Sample Before and After PBL Depletion | | | | |
|---|---|---|---|---|
| Initial % PBLs | % CD45 Positive Cells | % Cytokeratin Positive Cells | % PBLs Depleted | % Tumor Enrichment |
| 95 | 92.3 | 5.0 | — | — |
| DEPLETED SAMPLES | | | | |
| 5 | 1.7 | 98.1 | 82.3 | 3.3 |
| 25 | 1.3 | 98.0 | 94.3 | 22.3 |
| 75 | 0.8 | 99.5 | 98.8 | 69.6 |
| 95 | 0.6 | 99.4 | 99.3 | 95.0 |

FIGS. 4–7 are the single parameter histograms of the breast tumor cell samples containing 5, 25, 75 and 95% PBLs, respectively, both before and after PBL Depletion. The A and B figures are for undepleted samples and the C and D figures are for depleted samples. The A and C figures represent the total DNA present in the samples and the B and D figures represent the DNA of cytokeratin positive cells.

EXAMPLE 3

Samples representative of a breast tumor cell preparation containing infiltrating lymphocytes and normal fibroblasts were prepared containing 85% PBLs, 5% MDA-MB175-VII cells (breast tumor) and 10% WI-38 cells (normal fibroblast). As in the previous examples, a total of two sample sets are prepared, one to be the control (undepleted) and one for PBL depletion as described in Example 1. After depletion, aliquots of both sets are made ($10^6$ cells/tube). One aliquot from each set is stained with anti-cytokeratin-FITC, one with an anti-fibroblast monoclonal antibody which recognizes the WI-38 cells and is non-reactive with the MDA-MB-175-VII tumor cells and PBLs (indirect procedure), and one aliquot of each of these sets also stained with the control IgG1 antibody. All samples are then processed using the DNA-Prep® workstation. FIG. 8, A–D, are the flow cytometric histograms for the four samples—(A) undepleted, (B) PBL depleted, (C) PBL depleted, anti-cytokeratin treated and (D) PBL depleted, anti-fibroblast treated.

FIG. 8, A–D, again shows that the PBL may be depleted from the sample using an anti-CD45 monoclonal antibody conjugated to microspheres. Tumor cells are barely discernable in the DNA histogram of the undepleted sample, FIG. 8A, and thus are unable to be analyzed. However, after depletion of the PBLs, they are readily observed in the histogram, FIG. 8B. The histogram shows that the CD45 negative cells (the depleted samples) have two distinct cell populations or types, and that gated DNA using the anti-fibroblast monoclonal antibody leads to identification of the normal, diploid fibroblasts, FIG. 8D. Gated DNA analysis of the cytokeratin positive cells reveals the presence of about 15% S-phase cells and allows one to distinguish the $G_2/M$ peak of normal, cycling fibroblasts from the overlapping $G_0/G_1$ peak of breast tumor cells which have a DNA index near 2.0, FIG. 8C. Without using the gated analysis described herein, it would not be possible to distinguish these two cell populations or to measure the S-phase fraction.

EXAMPLE 4

Ideally, DNA analysis should be performed after flow cytometrically collecting a minimum of 10,000 total cell events for each sample. The higher the percentage of tumor cells within the sample, the greater will be the accuracy of the DNA analysis. When the tumor cells constitute a low percentage of total cells in a sample, a larger total number of cells must be counted, more than 10,000 than is the case when tumor cells are a relative high percentage of total cells. This, in turn, lengthens the analysis time and increases costs. Depletion of infiltrating cells, for example, PBLs, concentrates the tumor cells and thus permits processing of smaller sample in the DNA analysis. To further demonstrate the utility of PBL depletion, a sample containing 95% PBL and 5% MDA-MB-175-VII cells was prepared. One part of the sample was depleted as described herein and the remainder served as the control, nondepleted set. Aliquots from each set were processed for cytokeratin staining as previously described. A minimum of 10,000 events was collected. The results, shown in Table 3, indicate the utility of cell depletion for enriching a sample in tumor cells. To obtain the same number of tumor cell events as obtained using the depleted sample, approximately 200,000 cells would have to be processed if the sample were undepleted of PBLs.

TABLE 3

Number of Tumor Cells Collected Utilizing Cytokeratin Gated DNA Analysis Before and After PBL Depletion

| Sample No. | Total Number of Events Collected | Total Number of Tumor Cells Collected |
| --- | --- | --- |
| 1 (undepleted) | 10,000 | 501 |
| 2 (undepleted) | 42,000 | 1,872 |
| 3 (depleted) | 10,000 | 9869 |

EXAMPLE 5

A solid tumor sample (e.g., breast, colon, ovarian or brain, among others) is obtained by biopsy (for example) fine needle aspirate) or surgery and a cell suspension is prepared. The cell suspension is then processed according to the Examples herein with regard to PBL depletion, immunofluorescent staining with tumor or tissue associated marker such as a labelled monoclonal antibody and DNA stained. The sample is then analyzed by dual color flow cytometry using gated DNA analysis of the cells which are positive for expression of the tumor/tissue associated marker. The tumor cells are thereby segregated from other cells present in the sample, thus allowing for improved determination of ploidy and S-phase fraction.

EXAMPLE 6

A solid tumor sample is obtained as in Example 5 and made into a single cell suspension. After PBL depletion, the sample is stained with multiple markers to allow the determination of multiple cell types. For example, the markers may be labelled monoclonal antibodies or other substances reactive with tumor associated antigen, tissue associated antigen, oncogene and oncogene products and DNA. The number of possible combinations is limited only by the technical capabilities of the flow cytometer used and the reagents available, especially labelling dyes. The sample is then processed using gated DNA analysis to identify, for example, malignant breast cells in a breast tumor sample and the DNA of a selected subpopulation of those cells which express the estrogen receptor. Further subdivision is also feasible; for example, to predict the number of cells responsive to hormone therapy.

EXAMPLE 7

A peripheral blood sample from, for example, a chronic lymphocytic leukemia patient is depleted of erythrocytes by mixing with a magnetic microsphere bound, erythrocyte specific monoclonal antibody (KC-16, Coulter Corporation). After removal of the magnetic microspheres, the sample is slowly centrifuged to remove platelets. The platelet-free sample is then treated with a B cell specific monoclonal antibody (B1, Coulter Corporation) and DNA stained to enable gated DNA analysis of the tumor cells. Alternatively, using selected, labelled monoclonal antibodies to various leukemias and lymphomas, multiple color flow cytometry can be used to analyze the DNA of specific tumor cell populations.

EXAMPLE 8

A bladder washing is obtained which contains a large number of contaminating leukocytes and red blood cells (rbcs). The sample is first treated with KC-56 and KC-16 monoclonal antibodies bound to magnetic spheres to remove the leukocytes and rbcs. After further treating the sample as described herein, gated DNA analysis of cytokeratin positive cells is performed in order to determine ploidy and the S-phase fraction.

We claim:

1. A method for enriching the tumor cell fraction in a sample containing or thought to contain tumor cells and at least leukocytes, said method comprising:

(a) analyzing a first sample without leukocyte depletion by flow cytometry in order to determine DNA histogram;

(b) mixing a second sample with a pan-leukocyte monoclonal antibody conjugated to a separable substrate;

(c) separating the substrate and leukocytes conjugated thereto from said second sample, thereby specifically depleting said second sample of leukocytes and enriching the tumor cell fraction in said second sample;

(d) analyzing said depleted second sample by flow cytometry to determine the DNA histogram; and (e) comparing the peaks of the first sample with that of the second sample in order to determine the normal diploid peak and the DNA index of tumor peak.

2. The method according to claim 1 wherein said substrate is magnetic microspheres.

3. The method according to claim 1 wherein said monoclonal antibody is an anti-CD45 monoclonal antibody.

4. A method for determining the DNA ploidy and proliferation index of tumor cells in a suspension of single cells from a solid tumor or through to contain tumor cells and at least leukocytes, said method comprising:

(a) analyzing a first sample without leukocyte depletion by flow cytometry and measuring DNA polidy and proliferation;

(b) mixing a second sample with a pan-leukocyte monoclonal antibody conjugated to a separable substrate;

(c) separating the substrate and leukocytes conjugated thereto from said second sample, thereby specifically depleting said second sample of leukocytes;

(d) mixing said second sample with (1) a labeled monoclonal antibody specific to a tissue associated antigen arising from the presence of said tumor and (2) a DNA staining reagent; and (e) analyzing said second sample by flow cytometry for DNA containing cells by gating on the labelled tumor cells.

5. The method according to claim 4 wherein:

(a) when erythrocytes are present in the sample, before step (b) of claim 4, said sample is:

(i) treated with an erythrocyte specific monoclonal antibody conjugated to a separable substrate and said substrate and erthrocyte conjugated thereto are separated from said sample, or (ii) said erythrocytes are lysed and the debris is removed from said sample; and (b) when platelets are present in said sample, said platelets may be removed from said sample, preferably after step (b) and before step (c).

6. The method according to claim 4 wherein said substrate is magnetic microspheres.

7. The method according to claim 4 wherein said pan-leukocyte monoclonal antibody is an anti-CD45 monoclonal antibody.

8. The method according to claim 4 wherein the label of said labelled monoclonal antibody is a fluorescent label.

9. The method according to claim 4 wherein step (b) is deleted when said tumor cells arise from a CD45 positive leukemia or a lymphoma.

10. A method for determining the normal diploid peak and the DNA index of a tumor peak in a sample containing leukocytes and suspected of containing tumor cells, said method comprising the steps of:

(a) obtaining a DNA histogram from a sample containing leukocytes and suspected of containing tumor cells;

(b) incubating the sample with a pan-leukocyte monoclonal antibody conjugated to a separable substrate;

(c) separating the substrate from the sample, thereby specifically depleting the leukocytes conjugated to the substrate from the sample;

(d) obtaining a DNA histogram the depleted sample; and (e) comparing the DNA histogram to determine the normal diploid peak and the DNA index of the tumor peak.

11. The method according to claim 10 wherein said substrate is magnetic microspheres.

12. The method according to claim 10 wherein said monoclonal antibody is an anti-CD45 monoclonal.

13. A method for determining the DNA ploidy and proliferation index of tumor cells in a sample containing leukocytes and suspected of containing tumor cells, said method comprising the steps of:

(a) incubating a sample containing leukocytes and suspected of containing tumor cells with a pan-leukocyte monoclonal antibody conjugated to a separable substrate;

(b) separating the substrate from the sample thereby specifically depleting said sample of leukocytes;

(c) analyzing the depleted sample by gated DNA analysis to identify tumor cells; and (d) analyzing the tumor cells to determine the DNA ploidy and proliferation index of the tumor cells.

* * * * *